(12) United States Patent
Bäumler et al.

(10) Patent No.: US 9,381,162 B2
(45) Date of Patent: Jul. 5, 2016

(54) MICRO-PARTICLES, BLOOD-SUBSTITUTE AND METHOD FOR FORMING SAME (75) Inventors: Hans Bäumler, Berlin (DE); Radostina Georgieva, Berlin (DE)

(73) Assignee: CC-Ery GmbH, Berlin (DE)

( * ) Notice: Subject to any disclaimer, the term of this patent is extended or adjusted under 35 U.S.C. 154(b) by 250 days.

(21) Appl. No.: 12/668,876

(22) PCT Filed: Jul. 14, 2008

(86) PCT No.: PCT/EP2008/059192
§ 371 (c)(1),
(2), (4) Date: Apr. 5, 2010

(87) PCT Pub. No.: WO2009/010494
PCT Pub. Date: Jan. 22, 2009

(65) Prior Publication Data
US 2010/0209518 A1 Aug. 19, 2010

(30) Foreign Application Priority Data
Jul. 13, 2007 (EP) .................................... 07112474

(51) Int. Cl.
A61K 38/42 (2006.01)
A61K 35/16 (2015.01)
B32B 5/16 (2006.01)
A61K 9/50 (2006.01)
A61P 7/00 (2006.01)
B05D 7/00 (2006.01)
A61K 9/16 (2006.01)
A61K 9/00 (2006.01)
B01D 9/00 (2006.01)
B01J 13/14 (2006.01)
A61K 47/42 (2006.01)

(52) U.S. Cl.
CPC ............ *A61K 9/1694* (2013.01); *A61K 9/0026* (2013.01); *A61K 9/1611* (2013.01); *B01D 9/005* (2013.01); *B01J 13/14* (2013.01); *A61K 47/42* (2013.01); *Y10T 428/2982* (2015.01); *Y10T 428/2989* (2015.01); *Y10T 428/2991* (2015.01)

(58) Field of Classification Search
None
See application file for complete search history.

(56) References Cited

U.S. PATENT DOCUMENTS

| 5,069,936 | A  | * | 12/1991 | Yen .......................... 427/213.33 |
| 5,955,581 | A  |   | 9/1999  | Rausch et al. |
| 6,228,291 | B1 |   | 5/2001  | Lee et al. |
| 6,423,333 | B1 |   | 7/2002  | Stedronsky et al. |
| 6,914,127 | B2 |   | 7/2005  | Sehgal et al. |
| 2007/0184119 | A1 | * | 8/2007 | Suslick et al. ................ 424/491 |
| 2008/0020051 | A1 |   | 1/2008  | Dahne et al. |

FOREIGN PATENT DOCUMENTS

| WO | WO 94/20856 A1 | 9/1994 |
| WO | WO 00/53159 | 9/2000 |
| WO | WO 2005/089727 A1 | 9/2005 |

OTHER PUBLICATIONS

Petrov et al., "Protein-Calcium Carbonate Coprecipitation: A Tool for Protein Encapsulation", Biotechnol. Prog., 21, 2005, 918-925.*
Kreft et al. "Shell-in-Shell Microcapsules: A Novel Tool for Integrated, Spatially Confined Enzymatic Reactions", Angew. Chem. Int. Ed, 46, 2007, pp. 5605-5608. (Published online Jun. 21, 2007).*
Duan et al. "Hemoglobin protein hollow shells fabricated through covalen layer-by-layer technique", Biochemical and Biophysical Research Communications, 354, 2007, pp. 357-362. (Published online Jan. 10, 2007).*
Chang, T., "Therapeutic Applications of Polymeric Artificial Cells", Nature Reviews Drug Discovery, 4: 221-235 (2005).
Cölfen et al., "Geordnete mesoskopische Strukturen durch Selbstorganisation und Transformation von Hybrid-Nanostrukturen", Angew. Chem., 115: 2452-2468 (2003).
Duan et al., "Hemoglobin protein hollow shells fabricated through covalent layer-by-layer technique", Biochemical and Biophysical Research Communications, 354: 357-362 (2007).
Hosoda et al., "Template Effect of Crystalline Poly (vinyl alcohol) for Selective Formation of Aragonite and Vaterite CaCO3 Thin Films", Macromolecules, 36(17): 6449-6452 (2003).
Kato et al., "Effects of macromolecules on the crystallization of CaCO3 the Formation of Organic/Inorganic Composites", Supramolecular Science, 5: 411-415 (1998).
Kato, T., "Polymer/Calcium Carbonate Layered Thin-Film Composites", Adv. Mater., 12(20): 1543-1546 (2000).
Mann, S., "Die Chemie der Form", Angew. Chem., 112(19): 3532-3548 (2000).
Sakamoto et al., "Self-organization of Patterned CaCO3 /Polymer Composite Films: Tuning of Their Morphologies by the Change of Molecular Weights of Acidic Polymers", Chemistry Letters, 35(3): 310-311 (2006).
Shenoy et al., "Layer-by-Layer Engineering of Biocompatible, Decomposable Core-Shell Structures", Biomacromolecules, 4: 265-272 (2003).
Sugawara et al., "Aragonite CaCO3 thin-film formation by cooperation of Mg2+ and organic polymer matrices", Chem. Commun., 487-488 (2000).
Sugawara et al., "Self-Organized Calcium Carbonate with Regular Surface-Relief Structures", Angew. Chem. Int. Ed., 42: 5299-5303 (2003).

(Continued)

*Primary Examiner* — Bethany Barham
*Assistant Examiner* — Melissa Javier
(74) *Attorney, Agent, or Firm* — Leon R. Yankwich; David G. O'Brien; Yankwich & Associates, P.C.

(57) ABSTRACT

A method for forming micro-particles is provided. The method includes the steps of: —providing a first solution which includes at least an anion; —providing a second solution which includes at least a cation; —mixing the first solution with the second solution in presence of at least a first compound for forming porous templates, wherein the porous templates are formed by precipitation of a salt which includes the anion and the cation and wherein the first compound is at least partially incorporated in the porous templates; and—at least partially cross-linking the first compound in the porous templates.

10 Claims, 7 Drawing Sheets

(56) References Cited

OTHER PUBLICATIONS

Sugawara et al., "Self-Organization of Oriented Calcium Carbonate/Polymer Composites: Effects of a Matrix Peptide Isolated from the Exoskeleton of a Crayfish", Angew. Chem. Int. Ed., 45: 2876-2879 (2006).

Sugawara et al., "Assembled Structures of Nanocrystals in Polymer/Calcium Carbonate Thin-Film Composites Formed by the Cooperation of Chitosan and Poly(aspartate)", Journal of Polymer Science: Part A: Polymer Chemistry, 44: 5153-5160 (2006).

Sukhorukov et al., "Porous calcium carbonate microparticles as templates for encapsulation of bioactive compounds", J. Mater. Chem., 14: 2073-2081 (2004).

Volodkin et al., "Matrix Polyelectrolyte Microcapsules: New system for Macromolecule Encapsulation", Langmuir, 20: 3398-3406 (2004).

Volodkin et al., "Protein Encapsulation via Porous CaCO3 MicorparticlesTemplating", Biomacromolecules, 5: 1962-1972 (2004).

Wang et al., "Preparation of uniform sized chitosan microspheres by membrane emulsification technique and application as a carrier of protein drug", J. of Controlled Release, 106: 62-75 (2005).

Wang et al., "Combination of adsorption by porous CaCO3 microparticles and encapsulation by polyelectrolyte multilayer films for sustained drug delivery", Int. J. Pharmaceutics, 308: 160-167 (2006).

Fundueanu et al., "Physico-chemical characterization of Ca-alginate microparticles produced with different methods", *Biomaterials*, 20: 1427-1435 (1999).

Georgieva et al., "Permeability and Conductivity of Red Blood Cell Templated Polyelectrolyte Capsules Coated with Supplementary Layers", *Langmuir*, 20: 1895-1900 (2004).

Petrov et al., "Protein-Calcium Carbonate Coprecipitation: A Tool for Protein Encapsulation", *Biotechnol. Prog.*, 21: 918-925 (2005).

Goorha et al., "Artificial Blood", MJAFI, 59: 45-50 (2003).

US 5,484,894, 01/1996, Woiszwillo (withdrawn)

\* cited by examiner

MICRO-PARTICLES, BLOOD-SUBSTITUTE AND METHOD FOR FORMING SAME

CROSS REFERENCE TO RELATED APPLICATIONS

This application is a United States national stage filing under 35 U.S.C. §371 of international (PCT) application No. PCT/EP2008/059192, filed Jul. 14, 2008 and designating the US, which claims priority to European (EP) Application No. 07112474.7, filed Jul. 13, 2007.

This description describes embodiments pertaining to a method for forming micro-particles and in particular micro-particles which include at least one cross-linked compound. Further embodiments pertain to micro-particles.

BACKGROUND

Micro-particles are placed between nano-particles on the left and macroscopic particles on the right of the size scale. There are no sharp borders in both directions and the size range is mostly defined between 100 nm and 100 µm. Biological cells, for example, belong to the micro-particles if considered by size. Micro-particles are classified under different aspects: natural and synthetic; organic and inorganic; crystalline and amorphous; porous and non-porous; core-shell-, matrix- or homogeneous structure etc. The manufacturing methods for micro-particles are generally divided into top-down and bottom-up procedures. In the first case a macroscopic material is crashed by milling or high pressure homogenisation, in the second one, the particles are assembles from their molecular compounds by precipitation, crystallization, spray drying etc.

Furthermore, micro-particle assembling procedures mimicking biological processes have been developed in recent years. In generally, the particles are grown by interactive structuring of organic and inorganic materials by a so-called biomimetic process.

Some of the procedures described above allow the synthesis of micro-particles with a special inner structure. Typical examples are porous micro-particles with a vast inner surface due to the pores and cavities. A very interesting fine structure can be generated if the porous particles are used for assembling of complementary structures. The particles are then consisting of the porous template and the structure that fills the pores and cavities.

For a variety of applications, it is desired to produce a high quantity of micro-particles, which should have a well defined mean size. Further, the formed micro-particles should be stable to be stored for a long time. Easy and cost-efficient manufacture of micro-particles comprised of different compounds is also an ongoing desire.

BRIEF SUMMARY

In view of the above a method for forming micro-particles is provided which is simple, versatile and suitable for different materials. The micro-particles formed can be comprised of a single or of different materials or compounds and can be used for varying purposes.

According to an embodiment, a method for forming micro-particles is provided. The method includes:
  providing a first solution which includes at least an anion;
  providing a second solution which includes at least a cation;
  mixing the first solution with the second solution in presence of at least a first compound for forming porous templates, wherein the porous templates are formed by precipitation of a salt which includes the anion and the cation and wherein the first compound is at least partially incorporated in the porous templates; and
  at least partially cross-linking the first compound in the porous templates.

According an embodiment, a method for forming micro-particles is provided. The method includes:
  providing a suspension of porous templates and a solution which includes at least a first compound;
  mixing the solution with the suspension for at least partially incorporating the first compound in the porous templates; and
  with no further incorporation of a further compound in a separate step, at least partially cross-linking at least the first compound in the porous templates.

According to a further embodiment, a method for forming micro-particles is provided. The method includes:
  providing a first solution which includes at least an anion;
  providing a second solution which includes at least a cation;
  mixing the first solution with the second solution in presence of micro-templates and at least a first compound for forming porous templates which include the micro-templates as core, wherein the porous templates are formed by precipitation of a salt which includes the anion and the cation and wherein the first compound is at least partially incorporated in the porous templates; and
  at least partially cross-linking the first compound in the porous templates.

According to an embodiment, micro-particles are provided. The micro-particles includes:
  at least a first compound which is cross-linked; and
  a porous or spongy polymer network structure which is formed at least by the first compound.

According to an embodiment, a blood-substitute is provided which includes micro-particles which include a porous or spongy polymer network structure, which is formed at least by cross-linked haemoglobin. Unlike particles which are formed by cross-linking in a free solution and which are densely packed, the micro-particles as described herein are open-celled or open porous. The size of the micro-particles used as a blood-substitute can be in the range of about 1 µm to about 5 µm and typically in the range of about 2 µm to about 4 µm.

In some embodiments, porous templates are formed by precipitation of a salt in presence of a compound to be incorporated in the porous templates. The compound is provided in at least one of the first and the second solution or in both. During precipitation, the templates grow and cumulatively incorporate the compound. The compound can be provided in a high concentration which yields a high rate of incorporation so that the loading of the templates with the compound is high. In some embodiments, a mixture of compounds is incorporated in the growing porous templates. In further embodiments, at least two compounds are subsequently incorporated by a step-wise or repeating precipitation of the porous templates.

The cation and the anion are typically selected such that they form a salt which is poorly soluble in the solvent, which is typically an aqueous solution. The term "poorly soluble salt" as used in this description intends to describe that the salt is substantially not soluble in water so that the formed porous templates are substantially stable in water.

A further advantage is that templates filled with the compound and, after the optional dissolving of the templates, micro-particles comprised of the compound can be mass-produced to obtain large quantities of micro-particles.

Cross-linking of the compound incorporated in the porous templates allows an easy formation of polymers and avoids harsh conditions which would occur under normal polymerisation conditions, such as radical polymerisation. Therefore, polymers based on delicate compounds such as biomolecules, for example proteins and enzymes, can be formed under mild conditions which substantially do not affect the functioning of the compound. Hence, the cross-linked compound maintains its specific characteristic which makes the formed micro-particle suitable for applications which requires that the cross-linked compound maintains its specific function or activity (such as enzyme activity, oxygen adsorption and desorption capacity, drug activity, to name only few). Cross-linking of a mixture of compounds is also possible so that a polymer can be formed which is comprised of at least two different compounds.

Further, a polymer network structure can be formed which is sufficiently stable even after an optional dissolving of the porous templates. The polymer network structure also provides a large surface to volume ratio due to its large internal surface which is accessible after dissolving of the porous templates. Typically, the micro-particles have an open-cell or open-porous structure formed by the polymer network. Further compounds can be therefore adsorbed or coupled to the polymer network structure.

The size of the formed micro-particles can be adjusted for instance by controlling the precipitation process for forming the porous templates.

In some embodiments the templates are removed and only the templated fine structure remains as a network of thin cylinders, wires or tubes. Typical templates that are easily dissolvable are for example calcium carbonate, all calcium phosphates and silica.

BRIEF DESCRIPTION OF THE DRAWINGS

A full and enabling disclosure of the present invention, including the best mode thereof, to one of ordinary skill in the art, is set forth more particularly in the remainder of the description, including reference to the accompanying figures. Therein.

DESCRIPTION OF PREFERRED EMBODIMENTS

For purpose of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device and/or method, and such further applications of the principles of the invention as illustrated therein being contemplated as would normally occur now or in future to one skilled in the art to which the invention relates.

Figure 7:
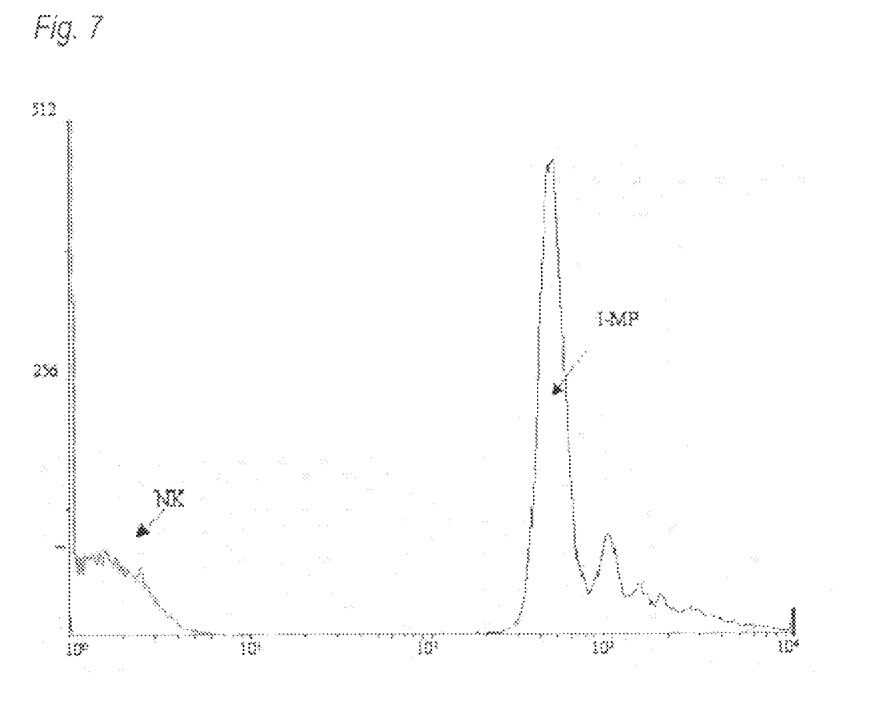
FIG. 7 shows a histogram of the fluorescence intensity of surface modified micro-particles prepared with albumin and attached insulin. NK: negative control; I-MP: insulin bearing micro-particles
Figure 8:
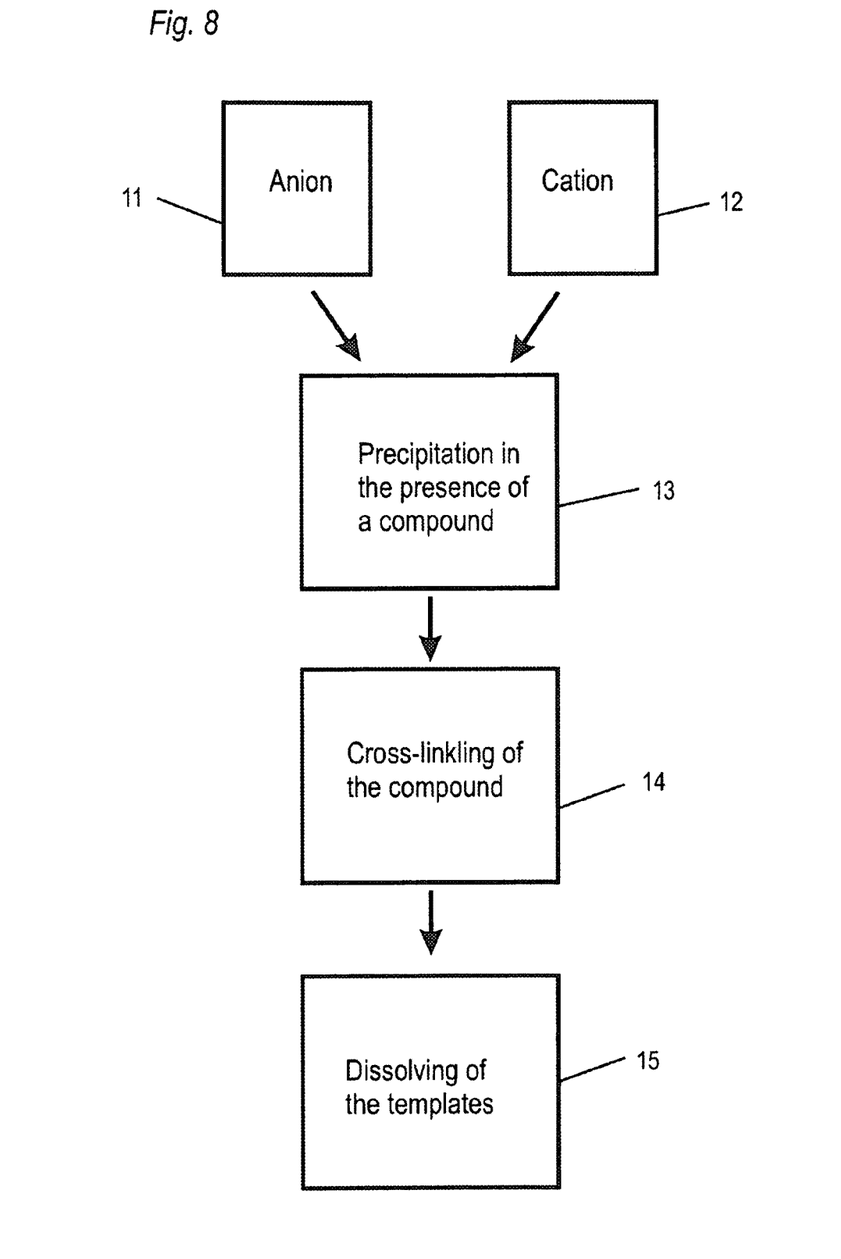
FIG. 8 illustrates sequences of a method for forming micro-particles.

An aspect of the present invention as described in this description is a method for forming micro-particles by precipitation of at least one salt in the presence of a compound or substance, wherein the precipitated salt forms templates into which the compound or substance is incorporated during growth of the templates. In an embodiment, as illustrated in FIGS. 7 and 8, a first solution 11 is provided which includes anions. Further, a second solution 12 which includes cations is provided. The anions and the cations are selected such that they allow the formation of a salt which is poorly soluble in an aqueous solution. The anions and the cations can be organic or inorganic. Typically, the anions are of inorganic nature and can be selected from the group containing Ca-ions, Mn-ions, Mg-ions, Ba-ions and mixtures thereof. Further, the cations are typically of inorganic nature and can be selected from the group containing carbonate-ions, phosphate-ions, hydrogen phosphate-ions, dehydrogen phosphate-ions, and mixtures thereof. For example, the first solution may comprise $CaCl_2$ for providing Ca-ions and the second solution $Na_2CO_3$ for providing carbonate-ions which results in the formation of $CaCO_3$ particles. A skilled person will appreciate that the cations and anions are not restricted to the above examples.

The cations and anions are further selected such that they allow the formation of porous templates by precipitation.

$CaCO_3$ particles are an example of porous templates. Other examples include, without being limited thereto, $MnCO_3$, all calcium phosphate particles, such as $Ca_3(PO_4)_2$, $CaHPO_4$ and $Ca(H_2PO_4)_2$, and $BaCO_3$.

A compound, which shall be incorporated into the porous templates to be formed, is provided in the first or the second solution 11, 12 or in both. Alternatively, a mixture of compounds can be provided in the first or the second solution or in both solutions. It is also possible to provide a compound in a first solution and another compound in the second solution, such that both compounds will be incorporated during precipitation. Providing the compounds in separate solutions helps to inhibit unwanted interactions between the compounds prior to incorporation.

Figure 9:
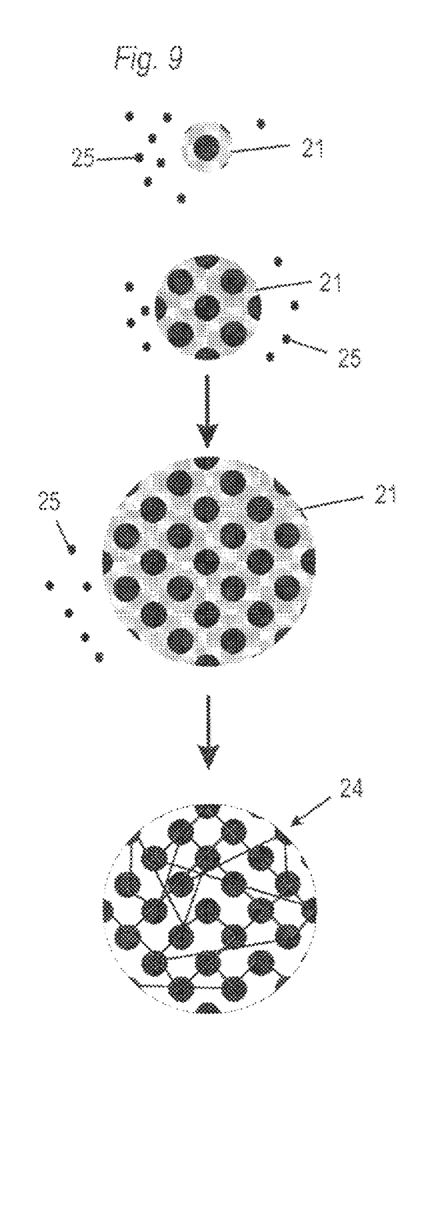
FIG. 9 illustrates the growing of the templates and the filling of the pores.

The first and the second solution 11, 12 are subsequently mixed (13). This initiates formation of templates 21 (FIG. 9) by precipitation of a poorly or even not soluble salt formed by the cations and anions. The precipitation takes place in the presence of the compound 25 (FIG. 9) or the compounds which will therefore be simultaneously and increasingly incorporated into the growing templates 21. The presence of the compound or compounds 25 may influence the crystallisation of the templates 21 and its structure. A natural porous structure of the templates facilitates the incorporation of the compound or the compounds. Since the pores of the templates can be completely filled by the compound or compounds 21 during growth a high compound to template ratio can be obtained which is typically substantially higher than the ration which can be obtained, when the compound 21 is incorporated subsequently to a complete formation of porous templates 21. FIG. 9 illustrates the growing of the templates 21.

The porous templates 21 will be typically formed by crystallisation. To initiate and/or control crystallisation, crystal seeds can be added to the mixture or to any or both of the first and second solution. The crystal seed can be for example very small particles comprised of the material of the porous templates. Porous templates, which have been prepared in advance or with other means, can also be used as seed crystals. This allows a step-wise formation of micro-particles for sequentially or step-wise incorporation of separate compounds.

An advantage of the "precipitation approach" as described herein is that a high loading of the templates and thus the micro-particles can be obtained. It is assumed that the compound or the mixture of compounds fills the pores of the growing templates. The templates are thus filled "from the inside to the outside" which allows a substantial complete loading of the templates.

Different thereto are other approaches which incorporate a compound in provided pre-formed porous templates. There, the compound is mixed with the pre-formed templates so that adsorption takes place after formation of the templates. Thus, the templates are filled "from the outside to the inside". Since adsorption starts at the outside of the templates and the entrance to the pores, the pores may become blocked and inhibit further loading of the templates with the compound so that the inner pores are not filled. In comparison with this approach the "precipitation approach" offers therefore a high loading rate independent of the type of the compound.

Figure 10:
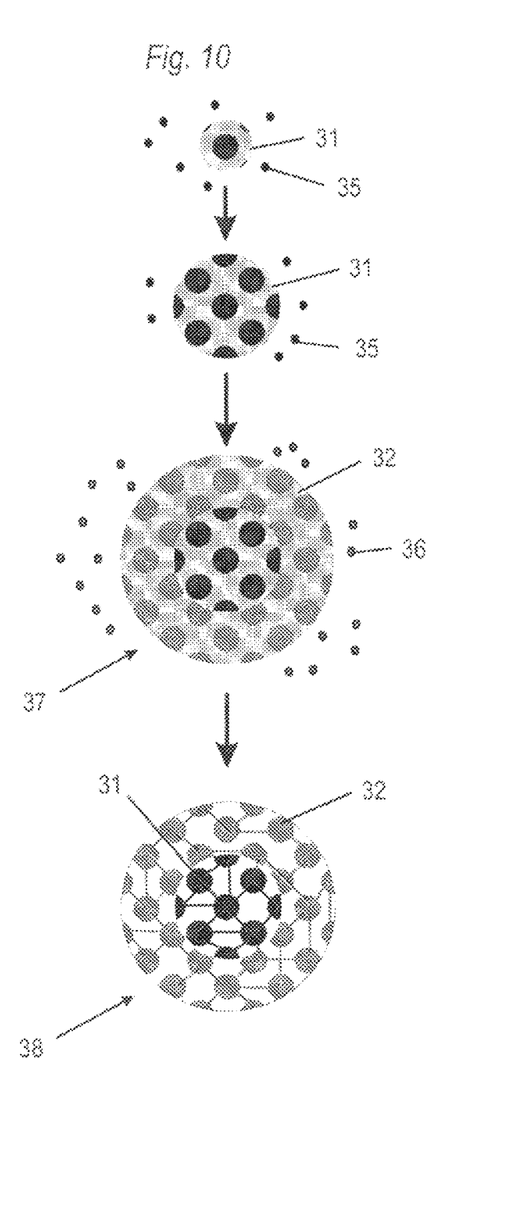
FIG. 10 illustrates the formation of a micro-particle comprising a core and a shell.

In some embodiments, which are illustrated in FIG. 10, porous templates 31 are formed in the presence of a first compound 35 or a first mixture of compounds by precipitation from a first mixture formed by mixing a first solution which includes anions and a second solution which includes. The porous templates 31 can be for instance formed by spontaneous crystallisation without any addition crystal seeds.

The thus formed porous templates 31 with the incorporated first compound 35 or first mixture of compounds are termed pre-templates. In a subsequent step, the pre-templates 31 can be used as seed crystals and are therefore brought in or mixed with a second mixture which is formed by mixing a third solution comprising anions with a fourth solution comprising cations. The second mixture also comprises a second compound 36 or a second mixture of compounds, which is provided in at least one of the third and fourth solution. The third and fourth solution may comprise the same anions and cations as the first and second solution. The pre-templates 31 cause or initiate crystallisation of a salt formed by the anions and cations of the second mixture on the surface of the pre-templates 31 which results in a formation of a shell 32 on the pre-templates 31. The second compound 36 or the second mixture of compounds is incorporated in the shell 32 growing on the pre-templates 31. Such formed templates 37 comprise a core 31 and a shell 32, each of which is filled with a specific compound or mixtures of compounds.

Spontaneous crystallisation may also occur in the mixture comprising the third and fourth solution but will lead to smaller porous templates which only include the second compound or the second mixture of compounds. These templates can easily be separated from the larger templates comprising the pre-templates by a suitable separation step such as filtration, sorting or centrifugation.

Basically, any porous particles or solid particles can be used as pre-templates to initiate formation of a shell which includes a compound or a mixture of compounds. Such porous or solid particles function as seed crystal for crystallisation of the shell.

The formation of a shell can be repeated if desired to form multiple shell layers each of which can include a specific compound or mixture of compounds. This allows a tailored manufacturing of micro-particles. For example, the compound or compounds of the outer shell are for protecting the compound or compounds of the inner shell (or shells) and the core. This approach also allows encapsulation of material by a compound or compounds that form a shell.

The pores of the micro-particles including the core and the shell can have a mean size (diameter) in the range of about 2 nm to about 50 nm.

In some embodiments, the compound or compounds included in the templates is cross-linked (Step 14 in FIG. 14). The cross-linking can be done after each precipitation step or at the end of the template formation. For example, different compounds may need different agents for cross-linking which opens the possibility to selectively cross-link the compounds. Further, the compound or compounds of the core and/or the shell or shells can be separately or simultaneously cross-linked. For cross-linking the compound or the compounds, an agent is used which typically has at least two functional groups. Such an agent is for instance a bi-functional agent. The cross-linking agent or agents can be selected, without being limited thereto, from table 1. Other cross-linking agents can also be used depending on the compound or compounds to be cross-linked. For instance, fixation solution used for fixating tissue would also be an option.

TABLE 1

| Name | Chemical Formula |
|---|---|
| Glutaraldehyde | $C_5H_8O_2$ |
| Divinylsulfone | $C_4H_6O_2S$ |
| Epichlorhydrin | $C_3H_5ClO$ |
| Cumolhydroperoxide | $C_6H_5C(CH_3)_2OOH$ |

TABLE 1-continued

| Name | Chemical Formula |
| --- | --- |
| Acetic acid | $C_2H_4O_2$/Methanol |
| Dimethylsuberimidate | $C_{10}H_{20}N_2O_2 \times 2ClH$ |
| Bis-(3,5 dibromosalicyl) fumarate | $C_{18}H_8Br_4O_8$ |
| Poly-(dimethylsiloxan) | $(C_2H_6OSi)_n$ |
| Formaldehyde | $CH_2O$ |
| Malondialdehyd-bis-(diethylacetal) | $C_{11}H_{24}O_4$ |
| Sebacyl chloride | Cl—CO—$(CH_2)_8$—CO—Cl |
| N-(3-dimethylaminopropyl)-N'-ethylcarbodiimide and N-hydroxysuccinimide | EDC and NHS |
| Thrombin | |
| Dibromobimane | $C_{10}H_{10}Br_2N_2O_2$ |
| Avidin/biotin | |

In some embodiments, the compound or the compounds can be activated or prepared for cross-linking prior to incorporation and precipitation. For example activated compounds are added to any of the salt solution for precipitation or added to the solution of preformed porous templates. Pre-activation can include, for example, breaking particular molecular bridges which are later used for cross-linking. In certain embodiments, dislufide-bridges of proteins can be broken by, for example, Dithiothreitol (DTT). Cross-linking is subsequently caused by oxygen or air. Another option is to bind appropriate groups or molecules to the compound or compounds to prepare them for cross-linking. An example is biotin which can be bound to a variety of compounds. Cross-linking is then caused by avidin.

The compound or compounds to be cross-linked need to have at least one functional group which can form, mediated by or with the cross-linking agent, a bound to other functional groups of the same or other types. Examples of functional groups are carboxylic, carbonylic, amino, hydroxylic, and sulfhydrilic groups.

By cross-linking the compound or compounds, a polymer network structure is formed in the porous templates. Depending on the compounds and the cross-linking agent or agents used, all compounds can be cross-linked with each other or can only selectively be cross-linked. Further, the compound 35 forming the core 31 and the compound 36 forming the shell 32 can be selectively or jointly cross-linked.

The compounds can be selected from the group which includes polymers, biomolecules, proteins, enzymes, nano-particles, pharmaceutical active compounds, nutrition supplements, and mixtures thereof. Specific examples include molecules which are capable of binding molecular oxygen such as haemeproteins, haemoglobin, myoglobin, albumin, and mixtures thereof. Other examples include molecules which are suitable of binding toxins or of initiating the in vivo formation of antibodies. A specific example for a toxin is saxitoxin.

Typically, the porous templates with the encapsulated compound or compounds can be washed before cross-linking to remove free compounds which were not incorporated in the templates. By doing so, substantially no cross-linked free compounds are formed which is of advantage for further optional steps such as purification and concentration of the templates. Further, after each precipitation/incorporation step, the obtained templates or pre-templates are typically separated from the mixture by suitable separation steps including washing, filtration and centrifugation.

In some embodiments, the porous templates 21, 37 are dissolved (step 15 in FIG. 8) after cross-linking to form micro-particles 24, 38 which are comprised of at least one cross-linked compound (FIGS. 9 and 10). The term "micro-particle", as used in this description, intends to describe particles which comprise a polymer network structure which have porous or spongy-like structure. The micro-particles 24, 28 are typically spherical but can be of any other shape like cubic, elliptic or rod-like. The micro-particles can have a size (diameter or largest extension) of at least 20 nm, particularly at least 100 nm and more particularly at least 500 nm. Further, the micro-particles can have a size of less than 50 μm, particularly less than 20 μm and more particularly less than 5 μm. In some embodiments, the micro-particles have a mean size between about 3 μm to about 5 μm.

The size of the formed templates 21, 37 and thus of the micro-particles 24, 38 is tuneable, without being limited thereto, by variation any of the following parameters: temperature, concentration of the salt solutions, the rate and duration of stirring during the process of crystallization, or a combination of these parameters.

Dissolving should be carried out in such an environment which does not or substantially does not affect the functioning and/or activity of the compounds. In case of $CaCO_3$ the templates can be readily solved by a chelating agent such as EDTA in mild conditions for most biomolecules.

The compounds to be incorporated typically have a molecular weight of at least 20 kDa, particularly of at least 30 kDa. It has been observed that compounds having a minimum molecular weight of at least 20 kDa form stable micro-particles after dissolving of the porous templates. For long-lasting or permanent incorporation of smaller compounds, i.e. compounds which have a molecular weight of less than 20 kDa, after dissolving of the porous templates, a mixture of at least a large compound having a molecular weight higher than 20 kDa and the small compound can be used. The large compound or compounds will form the "backbone" of the polymer network structure to which the small compound is linked.

In some embodiments, at least a first compound is incorporated into pre-prepared porous templates. To this end, porous templates are provided in a suspension which is mixed with a solution comprising at least the first compound. By allowing the first compound to be adsorbed in the templates for a given time, the porous templates are least partially filled with the compound. Here, the first compound is adsorbed after formation of the templates.

Two or more compounds can be incorporated by provided them together in the solution. If the adsorption is mediated by electrostatic interaction, the compounds should have the same charge to avoid electrostatic hindrance. This approach is a single step process where all compounds are incorporated in a single step. Without any further incorporation step, the incorporated compound or compounds are at least partially cross-linked as described above. The filled porous templates could be subsequently used as seed crystal for forming a shell on the filled porous templates as described above. Alternatively, the filled porous templates can be dissolved as described above to obtain micro-particles comprised of a polymer network structure as described above.

The porous templates used for the single-step process can be selected, without being limited thereto, from the group comprising $SiO_2$, carbonates, such as $CaCO_3$ and $MnCO_3$, phosphates, such as $Ca_3(PO_4)_2$, $CaHPO_4$, $Ca(H_2PO_4)_2$, and mixtures thereof.

Regardless their formation, the micro-particles can be labelled, functionalised and/or lyophilised. Labelling and functionalising can be done during incorporation, before or after dissolving of the templates. In some embodiments, the micro-particles are labelled and/or functionalised after dissolution of the templates to have easy access to all cross-linked compounds. Micro-particles with our without templates can be lyophilised Regardless their formation, the formed micro-particles or templates can be used for different purposes. An example is a drug-carrier. The pharmaceutical active drug can be either the cross-linked compound or a compound which is adsorbed on, or covalently bound to, the polymer network structure after dissolving the templates. When the drug is cross-linked, it will be released by in vivo cleavage of the linkage, which can be for instance enzymatically mediated. On the other hand, when the drug is adsorbed to the polymer network structure, it will be released by desorption, which can be for instance induced by changes of the physico-chemical environment.

In this description the term "pharmaceutical active drug" intends to describe a chemical entity which alters, inhibits, activates or otherwise affects biological events. For example, the drug includes, but is not limited to, anti-cancer substances, anti-inflammatory agents, immunosuppressants, anticoagulants, antrithrombotic agents, enzyme inhibitors, analgetic, antiproliferative agents, antimycotic substances, cytostatic substances, growth factors, hormones, steroids, non-steroidal substances, and anti-histamines.

In some embodiments, the micro-particles comprise a coating which encapsulates the micro-particles. The coating can be formed either prior to or after dissolving of the templates. Typically, the coating is formed prior to dissolving so that a substantially dense surface is available onto which the coating is formed. The coating can be formed by different methods such as deposition of polymers, lipids and/or poly-electrolytes.

A specific example refers to micro-particles which includes insulin which can be released in viva. Such micro-particles may include insulin, which was incorporated into the porous templates during the precipitation or by adsorption into pre-prepared porous templates. Then, a second precipitation with dextran containing solutions leads to a generation of a shell on and around the insulin containing micro-particle. The dextran in the shell is subsequently cross-linked and the porous template is dissolved. The release of entrapped insulin depends on the structure of the dextran shell.

Another specific example refers to micro-particles used as blood-substitute. Such micro-particles may include cross-linked haemoglobin which was incorporated into the porous templates during the precipitation or by adsorption into pre-prepared porous templates. The cross-linked haemoglobin forms a porous polymer network which typically has an open-cell structure and enables diffusion of solvent and oxygen. Such cross-linked haemoglobin micro-particles allow adsorption and desorption of oxygen which makes them suitable as a blood-substitute. By cross-linking, the micro-particles are substantially free of tetramer haemoglobin. Human or bovine, or any other, haemoglobin can be used.

The size of the haemoglobin micro-particles is typically in the range between about 1 µm and about 5 µm and particularly in the range between about 2 µm to about 4 µm. The polymer network formed by the cross-linked haemoglobin can have a molecular weight of at least 560 kDa. The blood-substitute typically further includes a physiological solution in which the micro-particles are dispersed. Alternatively, the micro-particles comprised of cross-linked haemoglobin can be provided as powder, such as lyophilisated particles, for dispersing in a physiological solution.

According to an embodiment, a kit is provided comprising a dry powder of cross-linked haemoglobin micro-particles and a physiological solution.

In addition to haemoglobin, the micro-particles can comprise a co-factor such as 2,3-DPG, for instance when human haemoglobin is used. Further, the haemoglobin micro-particles can also include enzymes such as red blood cell enzymes. Examples are carbonic anhydrase and catalase.

For manufacturing the haemoglobin micro-particles, the haemoglobin is incorporated during precipitation and growth of the templates. The haemoglobin can also be adsorbed into provided porous templates. The optional co-factor and/or enzymes can be incorporated into the templates during precipitation of the templates or adsorption together with the haemoglobin. It goes without saying that other compounds can also be incorporated into the haemoglobin micro-particles. The haemoglobin and the optional additional compounds (co-factor, enzymes and proteins) will be cross-linked.

The haemoglobin micro-particles can include a core and at least one shell. The core is typically comprised of cross-linked haemoglobin with optional co-factor, while the shell is comprised of a protein such as albumin. The optional enzymes can be in the core and/or the shell.

Additionally, the haemoglobin micro-particles can include a coating which encapsulates the micro-particles. The coating is typically formed prior to dissolving of the porous templates. Suitable coating materials are albumin or other proteins, dextrans, polyethylenoxids and polyethylenglycols of different molecular weights and lipids of different composition.

For manufacturing the cross-finked haemoglobin micro-particles, any of the methods described in this description can be used. A skilled person will appreciate that modifications might be required, which will, however, become apparent from the description. For completing the blood-substitute, the cross-linked haemoglobin micro-particles can be dispersed in a physiological solution which may include additional additives.

Basically, the micro-particles can be used as a carrier for a plurality of substances which can be adsorbed or otherwise bound to the open-cell or open-porous polymer network structure. Depending on the cross-linked compounds used, hydrophilic or hydrophobic substances can be incorporated into the micro-particles after dissolving of the templates.

The micro-particles can further be used as micro-catalyst or cosmetics.

In some embodiments, the micro-particles include a core and at least one shell, wherein each includes a different enzyme. Such micro-particles can form an enzyme-cascade such that a substance is step-wise enzymatically altered or modified by the respective enzymes. Micro-particles which includes two or more shells allow expansion of the cascade into three or more steps.

Now, specific examples will be described in conjunction with the Figures.

Example 1

Method for Forming Albumin Micro-Particles

Example 1 is a specific embodiment pertaining to the formation of micro-particles which include at least one cross-linked compound which is incorporated into porous templates during precipitation.

Initial solutions are $CaCl_2$, $Na_2CO_3$ and albumin (human, bovine . . . ). The $Na_2CO_3$ solution is provided in a proper pot. The albumin, which represents here the compound to be incorporated, is added to the $CaCl_2$ solution and the mixture is added to the $Na_2CO_3$ solution under continuous stirring. The final concentration of $CaCl_2$ and $Na_2CO_3$ was equal. The products of the procedure are albumin containing $CaCO_3$ particles (templates) and NaCl. The size of the albumin/$CaCO_3$ particles is tuneable by variation of temperature, the concentration of the salt solutions, the rate and/or duration of stirring during the process of crystallization. The formed particles (templates) are separated by centrifugation at 1000×g for 1 min and the supernatant is decanted. The pellet is then washed three times with distilled water in order to remove the excess of albumin in the suspension medium.

For cross-linking the well mixed packed particles are added to a solution of glutaraldehyde at a final concentration of 2% and incubated at room temperature for 1 hour. The incubation time can be varied if a different rate of cross-linking is desirable. The cross-linked albumin/$CaCO_3$ particles are then separated by centrifugation at 1000×g for 1 min and the supernatant is decanted. The pellet is then washed three times with distilled water in order to remove the excess of glutaraldehyde in the suspension medium.

Figure 1A:
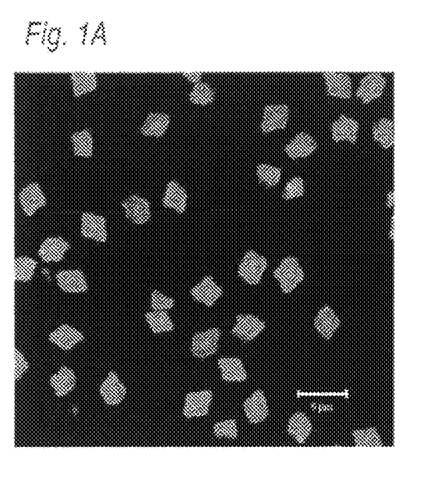
FIG. 1A shows a micrograph of cross-linked albumin micro-particles prepared at a low stirring rate for 1 min before rinsing. The sample contains 1% FITC-labelled albumin for better visualisation.
Figure 1B:
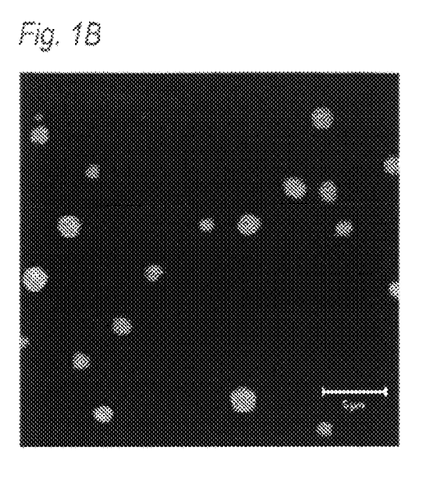
FIG. 1B shows a micrograph of cross-linked albumin micro-particles prepared at a high stirring rate for 20 sec before rinsing. The sample contains 1% FITC-labelled albumin for better visualisation.

Finally, the particles are added to a 0.2 M EDTA solution and the $CaCO_3$ crystals are dissolved. In this way, micro-particles of pure cross-linked albumin with a defined size are obtained (FIGS. 1A and 1B). The micro-particles are separated by centrifugation at 2000×g for 10 min and the supernatant is decanted. The pellet is then washed three times with distilled water in order to remove the excess of EDTA in the suspension medium. For allow better visualisation of the micro-particles and confirmation that the micro-particles internally comprised of albumin, 1% FITC-labeled albumin has been used. FIG. 1A shows cross-linked albumin particles prepared at a low stirring rate (about 1 $s^{-1}$ in this example) for 1 min before rinsing whereas FIG. 1B shows cross-linked albumin particles prepared at a high stirring rate (10 $s^{-1}$ in this example) for 20 sec before rinsing.

Example 2

Method for Forming Haemoglobin Micro-Particles

Example 2 is a specific embodiment pertaining to the formation of micro-particles suitable as a blood-substitute.

Initial solutions are $CaCl_2$, $Na_2CO_3$ and haemoglobin (isolated from e.g. mammalian red blood cells). The $CaCl_2$ solution is provided in a proper pot. The haemoglobin, which is the compound to be incorporated, is added to the $Na_2CO_3$ solution and the mixture is added to the $CaCl_2$ solution under stirring. The final concentration of $CaCl_2$ and $Na_2CO_3$ was equal. The products of the procedure are haemoglobin containing $CaCO_3$ particles (templates) and NaCl. The size of the hemoglobin/$CaCO_3$ particles is tuneable by variation of the temperature, concentration of the salt solutions, the rate and duration of stirring during the process of crystallization. The formed particles are then separated by centrifugation at 1000×g for 1 min and the supernatant is decanted. The pellet is then washed three times with distilled water in order to remove the excess of haemoglobin in the suspension medium.

For cross-linking, the well mixed packed particles (templates with incorporated haemoglobin) are added to a solution of glutaraldehyde at a final concentration of 2% and incubated at room temperature for 1 hour. The incubation time can be varied if a different rate of cross-linking is desirable. The cross-linked haemoglobin/$CaCO_3$ particles are separated by centrifugation at 1000×g for 1 min and the supernatant is decanted. The pellet is washed three times with distilled water in order to remove the excess of glutaraldehyde in the suspension medium.

Figure 2A:
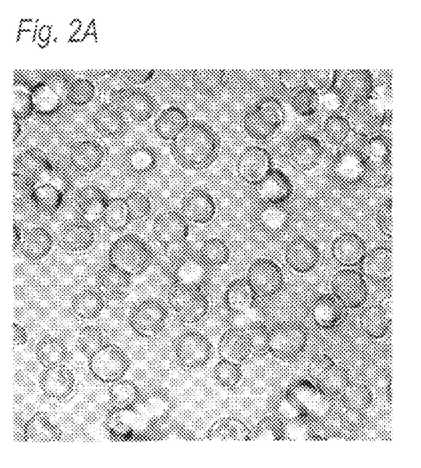
FIG. 2A shows a micrograph of cross-linked haemoglobin micro-particles prepared at a very low stirring rate for 2 min before washing.
Figure 2B:
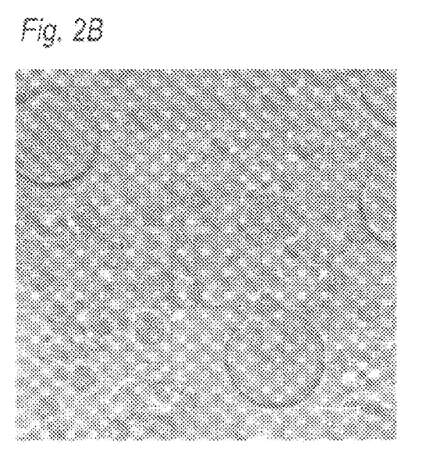
FIG. 2B shows a micrograph of cross-linked haemoglobin particles prepared at a medial stirring rate for 30 sec before washing.

Finally, the particles are added to a 0.2 M EDTA solution and the $CaCO_3$ crystals are dissolved. In this way micro-particles of pure cross-linked haemoglobin with a defined size are obtained (FIGS. 2A and 2B). The micro-particles are then separated by centrifugation at 2000×g for 10 min and the supernatant is decanted. The pellet is then washed three times with distilled water in order to remove the excess of EDTA in the suspension medium.

Figure 3:
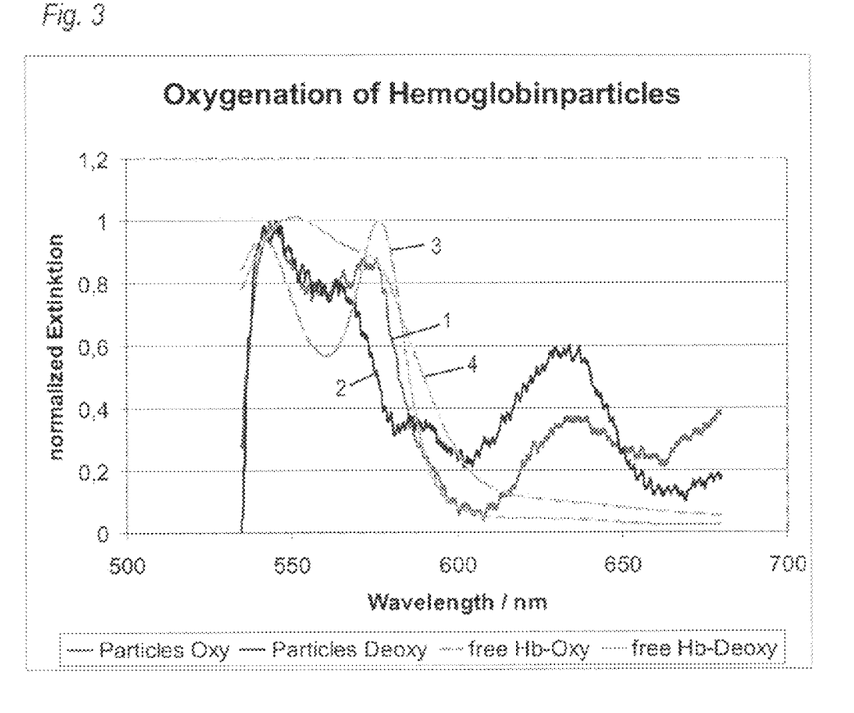
FIG. 3 shows a graph of the absorption spectra of cross-linked haemoglobin micro-particles at high and low $pO_2$. For comparison the spectra of oxy-haemoglobin and haemoglobin are displayed.

The cross-linked haemoglobin micro-particles showed the ability of reversible binding of oxygen as shown by the absorption spectra in FIG. 3, wherein 1 denotes oxygenated micro-particles and 2 deoxygenated micro-particles. For comparison the spectra of haemoglobin (4) and oxy-haemoglobin (3) are displayed. The oxygenated micro-particles ($pO_2$=17 kPa) showed the typical spectrum of oxy-haemoglobin. After exposure to $CO_2/N_2$ atmosphere for 20 min a $pO_2$ of 5 kPa was reached and the absorption of the haemoglobin micro-particle suspension altered to a typical deoxy-haemoglobin spectrum (4).

The spectra of the haemoglobin solution and haemoglobin particles were measured using a spectrophotometer (Hitachi K2800). The $pO_2$ and $pCO_2$ values were measured by means of a Blood Gas Analyzer (ABL 700, Radiometer).

FIG. 2A shows a micrograph of cross-linked haemoglobin micro-particles prepared at a low or very low stirring rate (about 0.5 $s^{-1}$ in this example) for 2 min before washing while FIG. 2B shows a micrograph of cross-linked haemoglobin particles prepared at a medium stirring rate (about 5 $s^{-1}$ in this example) for 30 sec before washing.

Example 3

Method for Preparation of Composite Haemoglobin/Albumin Micro-Particles

Example 3 is a specific embodiment pertaining to the formation of micro-particles which include a core and a shell each of which is comprised of a different compound.

Initial solutions are $CaCl_2$, $Na_2CO_3$, haemoglobin (isolated from mammalian red blood cells) and albumin. The $CaCl_2$ solution is provided in a proper pot. The haemoglobin is added to the $Na_2CO_3$ solution and the mixture is added to the $CaCl_2$ solution under stirring. The final concentration of $CaCl_2$ and $Na_2CO_3$ was equal. The products of the procedure are haemoglobin containing $CaCO_3$ particles and NaCl. The size of the haemoglobin/$CaCO_3$ particles is tuneable by variation of temperature, the concentration of the salt solutions, the rate and duration of stirring during the process of crystallization. The formed particles are then separated by centrifugation at 1000×g for 1 min and the supernatant is decanted. The pellet is then washed three times with distilled water in order to remove the excess of haemoglobin in the suspension medium.

The particles are then resuspended again in a $CaCl_2$ solution that contains albumin, and the $Na_2CO_3$ solution is added under stirring. The initiated new precipitation of $CaCO_3$ partially occurs on the surface of the existing particles leading to the generation of a shell containing albumin. The particles containing only albumin are separated by gradual density centrifugation or filtration based on their significantly smaller diameter.

For cross-linking, the well mixed packed particles are added to a solution of glutaraldehyde at a final concentration of 2% and incubated at room temperature for 1 hour. The incubation time can be varied if a different rate of cross-linking is desirable. The cross-linked hemoglobin/albumin/$CaCO_3$ particles are then separated by centrifugation at 1000×g for 1 min and the supernatant is decanted. The pellet is washed three times with distilled water in order to remove the excess of glutaraldehyde in the suspension medium.

The cross-linking reaction can also be performed after each precipitation step.

Finally, the particles are added to a 0.2 M EDTA solution and the $CaCO_3$ crystals are dissolved. In this way micro-particles of cross-linked haemoglobin with a shell of cross-linked albumin are obtained. The micro-particles are then separated by centrifugation at 2000×g for 10 min and the supernatant is decanted. The pellet is then washed three times with distilled water in order to remove the excess of EDTA in the suspension medium.

Figure 4:
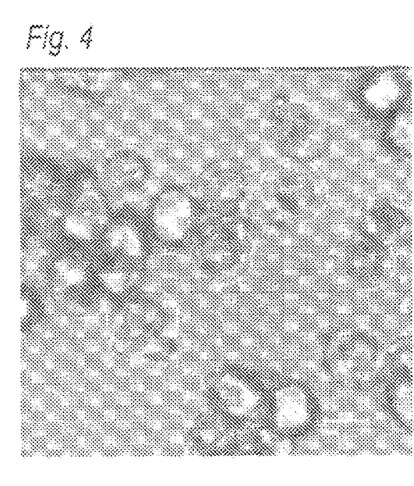
FIG. 4 shows a micrograph of cross-linked haemoglobin/albumin micro-particles prepared by two step precipitation. During the second precipitation step 1% FITC-labelled albumin (green) was added for better visualisation.

FIG. 4 shows a micrograph of such formed cross-linked haemoglobin/albumin micro-particles prepared by two step precipitation. During the second precipitation step 1% FITC-labelled albumin (green) was added for better visualisation. As becomes apparent from FIG. 4, the micro-particles comprises a fluorescent outer shell which is attributed to the albumin shell.

Example 4

Method for Preparation of Composite Trypsin/Albumin Micro-Particles

Example 4 is a specific embodiment pertaining to the formation of micro-particles which include a core and a shell of two different compounds.

Initial solutions are $CaCl_2$, $Na_2CO_3$, trypsin and albumin. The $Na_2CO_3$ solution is provided in a proper pot. The trypsin is added to the $CaCl_2$ solution and the mixture is added to the $Na_2CO_3$ solution under stirring. The final concentration of $CaCl_2$ and $Na_2CO_3$ was equal. The products of the procedure are trypsin containing $CaCO_3$ particles and NaCl. The size of the trypsin/$CaCO_3$ particles is tuneable by variation of temperature, the concentration of the salt solutions, the rate and duration of stirring during the process of crystallization. The formed particles are then separated by centrifugation at 1000×g for 1 min and the supernatant is decanted. The pellet is then washed three times with distilled water in order to remove the excess of trypsin in the suspension medium.

The particles are then resuspended again in a $CaCl_2$ solution that contains albumin, and the $Na_2CO_3$ solution is added under stirring. The initiated new precipitation of $CaCO_3$ partially occurs on the surface of the existing particles leading to the generation of a shell containing albumin. The particles containing only albumin are separated by gradual density centrifugation or filtration based on their significantly smaller diameter.

For cross-linking, the well mixed packed particles are added to a solution of glutaraldehyde at a final concentration of 2% and incubated at room temperature for 1 hour. The incubation time can be varied if a different rate of cross-linking is desirable. The cross-linked trypsin/albumin/$CaCO_3$ particles are then separated by centrifugation at 1000×g for 1 min and the supernatant is decanted. The pellet is washed three times with distilled water in order to remove the excess of glutaraldehyde in the suspension medium.

The cross-linking reaction can also be performed after each precipitation step.

Finally, the particles are added to a 0.2 M EDTA solution and the $CaCO_3$ crystals are dissolved. In this way micro-particles of cross-linked trypsin with a shell of cross-linked albumin are obtained. The micro-particles are then separated by centrifugation at 2000×g for 10 min and the supernatant is decanted. The pellet is then washed three times with distilled water in order to remove the excess of EDTA in the suspension medium.

Figure 5:
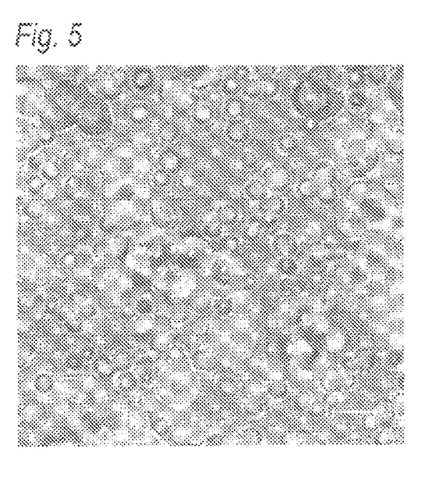
FIG. 5 shows a micrograph of cross-linked trypsin/albumin micro-particles prepared by two step precipitation. During the second precipitation step 1% FITC-labelled albumin (green) was added for better visualisation.

FIG. 5 shows a micrograph of cross-linked trypsin/albumin micro-particles prepared by two step precipitation. During the second precipitation step 1% FITC-labelled albumin (green) was added for better visualisation. As can be seen from FIG. 5, larger micro-particles comprising a non-fluorescent core and a fluorescent shell and smaller micro-particles, which merely comprise a fluorescent core, are formed. The smaller micro-particles were formed by spontaneous crystallisation of $CaCO_3$ in the albumin solution and thus do not comprise a trypsin core as the larger micro-particles. The core/shell micro-particles can be separated from the smaller micro-particles by any suitable separation technique.

Example 5

Method for Forming Dextran Particles

Example 5 is another specific embodiment pertaining to the formation of micro-particles which include at least one cross-linked compound.

Initial solutions are $CaCl_2$, $Na_2CO_3$ and dextran (MW 4 to 2500 kDa). The $Na_2CO_3$ solution is provided in a proper pot. The dextran is added to the $CaCl_2$ solution (the dextran concentration was varies from 2.5 to 10%) and the mixture is added to the $Na_2CO_3$ solution under continuous stirring. The final concentration of $CaCl_2$ and $Na_2CO_3$ was equal. The products of the procedure are dextran containing $CaCO_3$ particles and NaCl. The size of the dextran/$CaCO_3$ particles is tuneable by variation of temperature, the concentration of the salt and dextran solutions, the rate and duration of stirring during the process of crystallization. The formed particles are separated by centrifugation at 1000×g for 1 min and the supernatant is decanted. The pellet is then washed three times with distilled water in order to remove the excess of dextran in the suspension medium.

For cross-linking, the well mixed packed particles are re-suspended in 0.1 M NaOH and divinylsulfone (DVS) was added to final concentrations of 0.1 to 0.3% (v/v) and the samples were incubated under stirring at room temperature for 2 hours.

Finally, the particles are added to a 0.2 M EDTA solution and the $CaCO_3$ crystals are dissolved at room temperature within 20 min. In this way micro-particles of pure cross-linked dextran with different size distributions are obtained (FIGS. 6A to 6E). The particles are separated by centrifugation at 2000×g for 10 min and the supernatant is decanted. The pellet is then washed three times with distilled water in order to remove the excess of EDTA in the suspension medium. The optimal DVS concentration for particles with a size from 2 to 10 μm was 0.1% (v/v).

Figure 6A:
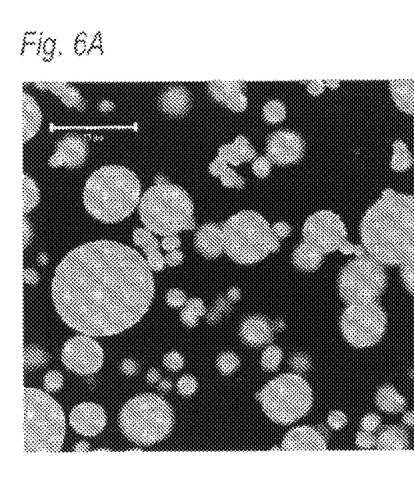
FIG. 6A shows a micrograph of cross-linked dextran micro-particles prepared with FITC labelled dextran having a molecular weight of about 64 to about 76 kDa.
Figure 6B:
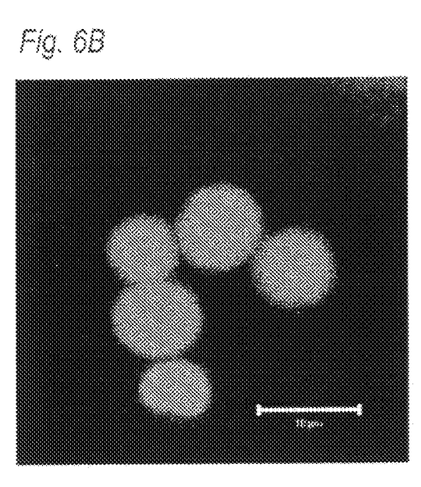
FIG. 6B shows a micrograph of cross-linked dextran micro-particles prepared with FITC labelled dextran having a molecular weight of about 564 kDa.
Figure 6C:
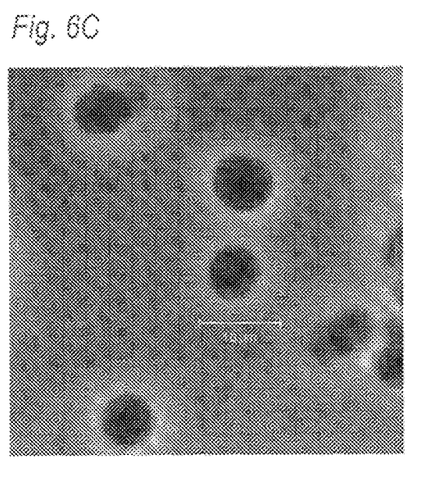
FIG. 6C shows a micrograph of cross-linked dextran micro-particles prepared with FITC labelled dextran having a molecular weight of about 64 to 67 kDa.
Figure 6D:
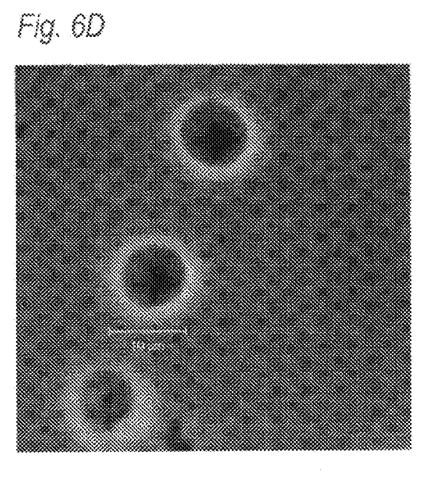
FIG. 6D shows a micrograph of cross-linked dextran micro-particles prepared with dextran having a molecular weight of about 464 kDa.
Figure 6E:
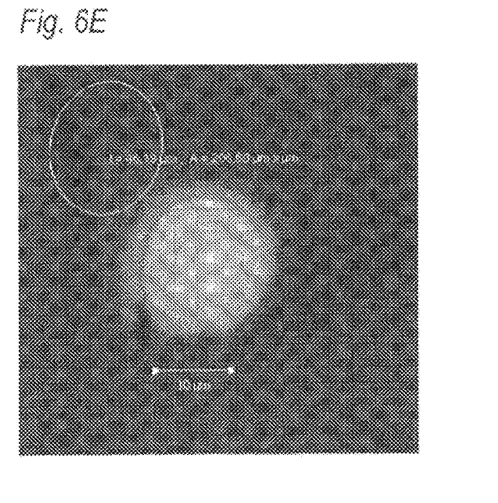
FIG. 6E shows a micrograph of cross-linked dextran micro-particles prepared with FITC labelled dextran having a molecular weight of about 464 kDa.

FIG. 6A shows a micrograph of cross-linked dextran micro-particles prepared with FITC labelled dextran having a molecular weight of about 64 to about 76 kDa. FIG. 6B shows a micrograph of cross-linked dextran micro-particles prepared with FITC labelled dextran having a molecular weight of about 564 kDa. FIG. 6C shows a micrograph of cross-linked dextran micro-particles prepared with FITC labelled dextran having a molecular weight of about 64 to 67 kDa. FIG. 6D shows a micrograph of cross-linked dextran micro-particles prepared with dextran having a molecular weight of about 464 kDa. FIG. 6E shows a micrograph of cross-linked dextran micro-particles prepared with FITC labelled dextran having a molecular weight of about 464 kDa.

Example 6

Method for Forming Albumin Micro-Particles

Example 6 is a specific embodiment pertaining to the formation of micro-particles which include at least one cross-linked compound by incorporating the compound into pre-prepared porous templates.

Initial solutions are $CaCl_2$, $Na_2CO_3$ and albumin (human, bovine . . . ). The $Na_2CO_3$ solution is provided in a proper pot and the $CaCl_2$ solution is added under continuous stirring. The final concentration of $CaCl_2$ and $Na_2CO_3$ was equal. The products of the procedure are porous $CaCO_3$ particles and NaCl. The size of the $CaCO_3$ particles is tuneable by variation of temperature, the concentration of the salt solutions, the rate and duration of stirring during the process of crystallization. The formed particles are separated by centrifugation at 1000×g for 1 min and the supernatant is decanted. The pellet is then washed three times with distilled water.

The washed particles are then resuspended in an aqueous solution of albumin and the suspension is incubated under stirring for 1 hour to allow adsorption of the protein in the pores of the particles.

For cross-linking the well-mixed packed particles are added to a solution of glutaraldehyde at a final concentration of 2% and incubated at room temperature for 1 hour. The incubation time can be varied if a different rate of cross-linking is desirable. The cross-linked albumin/$CaCO_3$ particles are then separated by centrifugation at 1000×g for 1 min and the supernatant is decanted. The pellet is then washed three times with distilled water in order to remove the excess of glutaraldehyde in the suspension medium.

Finally, the particles are added to a 0.2 M EDTA solution and the $CaCO_3$ crystals are dissolved. In this way micro-particles of pure cross-linked albumin with a defined size are obtained. The micro-particles are separated by centrifugation at 2000×g for 10 min and the supernatant is decanted. The pellet is then washed three times with distilled water in order to remove the excess of EDTA in the suspension medium.

Example 7

Method for Attachment of Peptides and Proteins on the Surface of Cross-Linked Polymeric Micro-Particles Example 7 describes a specific embodiment pertaining the modification, functionalising and/or coating of the surface of micro-particles.

Proteins and peptides have been attached to micro-particles prepared according to any of the examples 1 to 6 using avidin/biotin coupling. For this purpose the micro-particles are first coupled to biotin (1 mg sulfo-NHS-LG-biotin in PBS per $10^8$ particles) by incubation at room temperature for 1 hour. Then the micro-particles are washed three times with PBS to remove excess of biotin.

The biotin-coupled micro-particles are then re-suspended in PBS containing avidin (50 µg per $10^8$ particles) and incubated under stirring for 1 hour (room temperature) and finally washed 3 times in PBS. Now biotin-coupled peptides, proteins, DNA etc. $NH_3$-bearing molecules can be attached on the surface of the particles. The coupling of the molecules was quantified by means of flow-cytometric measurements (FIG. 7) using FITC-labelled avidin or biotin (NK: negative control; I-MP: insulin bearing micro-particles).

Example 8

Method for Attachment of Polyethylene Glycol on the Surface of Cross-Linked Polymeric Micro-Particles Example 8 describes another specific embodiment pertaining the modification, functionalising and/or coating of the surface of micro-particles.

The surface of micro-particles prepared according to any of the examples 1 to 6 was modified by covalent attachment of PEG (MW 2 to 20 000). For this purpose the micro-particles were re-suspended in a solution of 20 mg/ml methoxy-polyethylene glycol (mPEG) in 0.1 M borate buffer pH 9 and incubated under stirring at room temperature for 1 hour. Three washing steps with distilled water finished the procedure.

The bonding of PEG on the micro-particles was confirmed by zeta-potential measurements (Nanosizer 3000, Malvern, U. K.) with PEG-modified particles having a significant lower zeta-potential. For example, the zeta-potential value of the non-modified Hb-particles was 28±5 mV as measured in pure distilled water (conductivity 0.01 to 0.03 mS/cm). The PEG-modified Hb-particles showed a potential of only 9±3 mV as measured under similar conditions.

While preferred embodiments have been illustrated and described in detail in the drawings and foregoing description, the same is to be considered as illustrative and not restrictive in character, it being understood that only the preferred embodiment has been shown and described and that all changes and modifications that comes within the spirit of the invention both now or in the future are desired to be protected.

Example 9

Method for Forming Polymer/Protein Micro-Particles by Oxygen Cross-Linking

Example 9 is a specific embodiment pertaining to the formation of micro-particles which include at least one cross-linked compound which is incorporated into porous templates formed during precipitation. The cross-linked compound can be a protein and/or a polymer. In this example, the protein/polymer-particles are formed in a single step, wherein cross-linking occurs subsequently. Different to example 1, the compound is activated prior to precipitation, and is cross-linked by oxygen.

Initial solutions are $CaCl_2$, $Na_2CO_3$ and a protein, polymer or monomer solution or a mixture of any of the protein, polymer and monomer. The protein, polymer or monomer, which represents here the compound to be incorporated, is activated. In case of proteins, Dithiothreitol (DTT) can be used for activation. DTT breaks disulfide-bridges. The activated compound is added to either of the $Na_2CO_3$ and $CaCl_2$ solution. Then, this mixture is mixed with the other of the $Na_2CO_3$ and $CaCl_2$ solution. For example, the $Na_2CO_3$ solution with the added activated compound can be provided in a proper pot and then the $CaCl_2$ solution is added thereto under continuous stirring. The final concentration of $CaCl_2$ and $Na_2CO_3$ is roughly equal. During mixing, precipitation with simultaneous incorporation of the activated compound occurs. The products of the procedure are compound (for example albumin) containing $CaCO_3$ particles (templates) and NaCl. The size of the compound/$CaCO_3$ particles is tuneable by variation of any one of temperature, the concentration of the salt solutions, the rate and/or duration of stirring during the process of crystallization/precipitation. The formed particles (templates) are separated by centrifugation at 1000×g for 1 min and the supernatant is decanted. The pellet can then be washed three times with distilled water in order to remove the excess of compound in the suspension medium.

Alternatively or subsequently, the pellet can also be resuspended in water or in an HCl solution with moderate mixing. At the same time, air or oxygen can be introduced into the solution for cross-linking the activated compound. The duration of this step and the amount of air/oxygen feed through the solution determine the cross-linking level.

Finally, the particles are added to a 0.2 M EDTA solution and the $CaCO_3$ crystals are dissolved at room temperature within 20 min. In this way micro-particles of cross-linked compound are obtained. The particles are separated by centrifugation at 2000×g for 10 min and the supernatant is decanted. The pellet is then washed three times with distilled water in order to remove the excess of EDTA in the suspension medium. In case of albumin, cross-linked albumin micro-particles are formed.

Example 10

Method for Forming Albumin/Haemoglobin Micro-Particles by Oxygen Cross-Linking

Example 10 is a specific embodiment pertaining to the formation of micro-particles which include albumin and haemoglobin wherein the albumin is activated before precipitation. The activation and formation of the micro-particles can be done as described in example 9.

Initial solutions are $CaCl_2$, $Na_2CO_3$, an albumin solution, and a haemoglobin solution. Albumin is activated using Dithiothreitol (DTT) as described above. The activated albumin is added to either of the $Na_2CO_3$ and $CaCl_2$ solution. The haemoglobin solution is added to the other of the $Na_2CO_3$ and $CaCl_2$ solution and then both solutions are mixed under continuous stirring. The final concentration of $CaCl_2$ and $Na_2CO_3$ is usually equal. During mixing, precipitation with increasing incorporation of haemoglobin and activated albumin occurs. The products of the procedure are albumin/haemoglobin containing $CaCO_3$ particles and NaCl. The formed particles are separated by centrifugation at 1000×g for 1 min and the supernatant is decanted. The pellet is then washed three times with distilled water in order to remove the excess of compound in the suspension medium.

Alternatively or subsequently, the pellet can also be resuspended in water or in an HCl solution with moderate mixing. At the same time, air or oxygen is introduced into the solution for cross-linking the activated albumin wherein the albumin also cross-links with haemoglobin. The duration of this step and the amount of air/oxygen feed through the solution determine the cross-linking level.

Finally, the particles are added to a 0.2 M EDTA solution and the $CaCO_3$ crystals are dissolved at room temperature within 20 min. In this way micro-particles of cross-linked albumin/haemoglobin are obtained. The particles are separated by centrifugation at 2000×g for 10 min and the supernatant is decanted. The pellet is then washed three times with distilled water in order to remove the excess of EDTA in the suspension medium.

Example 11

Method for Forming Cross-Linked Plasma Micro-Particles

This example differs from example 1 in the use of blood plasma instead of albumin, wherein the blood plasma is cross-linked using thrombin. Hence, this specific example pertains to the formation of micro-particles which include cross-linked plasma.

Initial solutions are $CaCl_2$, $Na_2CO_3$ and blood plasma (human, bovine . . . ). The $Na_2CO_3$ solution is provided in a proper pot. The blood plasma, which represents here the compound to be incorporated, is added to the $CaCl_2$ solution and the mixture is added to the $Na_2CO_3$ solution under continuous stirring. The final concentration of $CaCl_2$ and $Na_2CO_3$ is substantially equal. Plasma containing $CaCO_3$ particles are formed by precipitation. The formed particles (templates) are separated by centrifugation at 1000×g for 1 min and the supernatant is decanted. The pellet is then washed three times with distilled water in order to remove the excess of albumin in the suspension medium.

For cross-linking, thrombin is added to the well mixed particles in a concentration of about 8 IU/ml and incubated at room temperature for 20 min at 37° C. 1 IU (international unit) corresponds to about 0.0583 mg Thrombin; 8 IU to about 0.4664 mg Thrombin. Thrombin causes cross-linking of the fibronectin contained in the blood plasma. The incubation time and/or the temperature can be varied if a different rate of cross-linking is desirable. By selecting the temperature and/or the incubation time, the characteristics of the formed particles, for example the density of cross-linking, can be adjusted. The cross-linked blood plasma/$CaCO_3$ particles are then separated by centrifugation at 1000×g for 1 min and the supernatant is decanted. The pellet is then washed three times with distilled water in order to remove the excess of thrombin in the suspension medium.

Finally, the particles are added to a 0.2 M EDTA solution and the $CaCO_3$ particles are dissolved. In this way, micro-particles of cross-linked blood plasma with a defined size are obtained as shown in FIGS. 1A and 1B for example 1. The micro-particles are separated by centrifugation at 2000×g for 10 min and the supernatant is decanted. The pellet is then washed three times with distilled water in order to remove the excess of EDTA in the suspension medium.

By this process, hollow or spongy-like blood plasma micro-particles are formed which can include other compounds if they were added during precipitation or contained in any of the slat solutions. For example, peptides can be added which become trapped in the blood plasma micro-particles.

Example 12

Method for Forming Micro-Particles which Include Biotinylated Compounds

The example refers to a method for forming micro-particles which include biotinylated compounds selected from proteins, DNA, RNA, peptides, anti bodies, anti genes, biopolymers and mixtures thereof. These compounds can be incorporated into the porous particles by precipitation as described above in any of the examples including adsorption into provided porous particles.

Different to the other examples, cross-linking is done using avidin which cross-links with biotin of the biotinylated compounds. The compounds can either be provided in their biotinylated form or can be biotinylated in a preceding step. The concentration of, and the ratio between, avidin and biotin determine the cross-linking level. For example, the ratio between biotin to avidin can be about 5:1. A specific example is biotinylated albumin. When using biotinylated albumin, about 16 μmol biotin and about 3 μmol are used. A skilled person will appreciate that other compounds may require other ratios.

After dissolution of the porous templates as described above, micro-particles are obtained which can include peptides, DNA, RNA or other compounds.

The invention claimed is:

1. A method for forming a blood substitute comprising micro-particles, the method comprising:
   providing a first solution comprising at least an anion;
   providing a second solution comprising at least a cation;
   mixing the first solution with the second solution in the presence of at least a first compound selected from the group comprising haemeproteins, hemoglobin, myoglobin, and mixtures thereof;
   forming porous templates, wherein the porous templates are formed by precipitation of a salt comprising the anion and the cation and wherein the first compound is at least partially incorporated within the forming porous templates; and
   forming within the porous templates an open porous or open polymer network structure by reacting, after precipitation, a cross-linking agent with the first compound incorporated within the porous templates to crosslink said first compound within the porous templates, wherein the cross-linked first compound of the polymer network structure is capable of adsorbing and desorbing oxygen.

2. The method according to claim 1, further comprising:
   providing a third solution comprising at least an anion;
   providing a fourth solution comprising at least a cation;
   mixing the third solution with the fourth solution in the presence of the porous templates and at least a second compound so that the porous templates grow by precipitation of a salt comprising the anion and the cation, wherein the second compound is at least partially incorporated within the porous templates, and
   forming within the porous templates an open porous or open polymer network structure by reacting, after precipitation, a cross-linking agent with the second compound incorporated within the porous templates to crosslink said second compound within the porous templates.

3. The method according to claim 2, wherein the steps of cross-linking the first and the second compound are performed in a single step.

4. The method according to claim 1 or claim 2, further comprising: dissolving the porous templates to form microparticles comprised at least of the cross-linked first compound or the cross-linked first and second compound.

5. The method according to claim 1 or claim 2, wherein the anions of the first and third solution are selected from the group comprising carbonate-ions, phosphate-ions, hydrogen phosphate-ions, dihydrogen phosphate-ion, and mixtures thereof.

6. The method according to claim 1 or claim 2, wherein the cations of the second and fourth solution are selected from the group comprising Ca-ions, Mn-ions, Mg-ions, Ba-ions, and mixtures thereof.

7. The method according to claim 1 or claim 2, further comprising: washing the porous templates before cross-linking the first and/or the second compound.

8. The method according to claim 1 or claim 2, further comprising: binding antibodies and/or antigens to the micro-particles.

9. The method according to claim 4, wherein dissolving the porous templates comprises forming the micro-particles having a size between about 500 nm and 5 μm.

10. The method according to claim 1, wherein mixing the first solution with the second solution comprises:
    mixing the first solution with the second solution in the presence of at least the first compound selected from the group comprising haemeproteins, hemoglobin, myoglobin, and mixtures thereof, and in the presence of at least a second compound selected from the group comprising co-factors, enzymes, proteins, and mixtures thereof; and
    wherein forming within the porous templates the open porous or open polymer network structure comprises:
    forming within the porous templates an open porous or open polymer network structure by reacting, after precipitation, the cross-linking agent with the first compound and the second compound incorporated within the porous templates to crosslink said first compound and said second compound within the porous templates, wherein the open porous or open polymer network structure comprises the first compound and the second compound which are cross-linked with each other, wherein the cross-linked first compound of the polymer network structure is capable of adsorbing and desorbing oxygen.

* * * * *